(12) United States Patent
Banju

(10) Patent No.: US 7,273,450 B2
(45) Date of Patent: Sep. 25, 2007

(54) STEREOSCOPIC OBSERVATION SYSTEM

(75) Inventor: Kazuo Banju, Tokyo (JP)

(73) Assignee: Olympus Corporation (JP)

( * ) Notice: Subject to any disclaimer, the term of this patent is extended or adjusted under 35 U.S.C. 154(b) by 403 days.

(21) Appl. No.: 10/814,976

(22) Filed: Mar. 31, 2004

(65) Prior Publication Data

US 2004/0210106 A1    Oct. 21, 2004

(30) Foreign Application Priority Data

Mar. 31, 2003    (JP)    ............... 2003-096165

(51) Int. Cl.
*A61B 1/00* (2006.01)
(52) U.S. Cl. .................... 600/102; 606/130
(58) Field of Classification Search ............... 600/102, 600/111, 166; 606/1, 130; 248/122.1, 124.1
See application file for complete search history.

(56) References Cited

U.S. PATENT DOCUMENTS

| | | | | |
|---|---|---|---|---|
| 5,173,802 A | * | 12/1992 | Heller | 359/384 |
| 5,689,365 A | * | 11/1997 | Takahashi | 359/362 |
| 5,776,049 A | * | 7/1998 | Takahashi | 600/111 |
| 5,907,664 A | * | 5/1999 | Wang et al. | 700/251 |
| 6,102,850 A | * | 8/2000 | Wang et al. | 600/102 |
| 6,120,433 A | * | 9/2000 | Mizuno et al. | 600/102 |
| 6,142,931 A | * | 11/2000 | Kaji | 600/114 |
| 6,514,239 B2 | * | 2/2003 | Shimmura et al. | 606/1 |
| 6,569,084 B1 | * | 5/2003 | Mizuno et al. | 600/102 |
| 2004/0138524 A1 | * | 7/2004 | Ueda et al. | 600/102 |
| 2004/0172012 A1 | * | 9/2004 | Otsuka et al. | 606/1 |
| 2005/0256371 A1 | * | 11/2005 | Schara et al. | 600/102 |

FOREIGN PATENT DOCUMENTS

JP    7-20388    1/1995

* cited by examiner

*Primary Examiner*—John P. Leubecker
(74) *Attorney, Agent, or Firm*—Ostrolenk, Faber, Gerb & Soffen, LLP

(57) ABSTRACT

A stereoscopic observation system includes a stereoscopic optical unit and stereoscopic camera. The optical unit is provided with a pair of objectives for stereoscopic observation and optical devices corresponding to the respective objectives. The stereoscopic camera is connected to the stereoscopic optical unit and used to pick up optical images formed by the optical devices. At least one of the stereoscopic camera and the optical unit serves as an instrument to be supported. A support unit supports the instrument. A rotation mechanism is incorporated in the support unit, and has a rotary shaft substantially parallel to an optical axis of the objectives. The rotation mechanism supports the instrument such that the instrument can rotate about the axis of the rotary shaft.

5 Claims, 4 Drawing Sheets

STEREOSCOPIC OBSERVATION SYSTEM

CROSS-REFERENCE TO RELATED APPLICATIONS

This application is based upon and claims the benefit of priority from the prior Japanese Patent Application No. 2003-96165, filed Mar. 31, 2003, the entire contents of which are incorporated herein by reference.

BACKGROUND OF THE INVENTION

1. Field of the Invention

The present invention relates to a stereoscopic observation system used, during a surgical operation using an endoscope, for stereoscopic observation of a to-be-operated-on portion in the body cavity of a patient.

2. Description of the Related Art

In general, in surgical operations utilizing endoscopic observation, a stereoscopic endoscope is often used which three-dimensionally displays an image. In this case, a surgeon performs an operation while observing a stereoscopic image generated by the stereoscopic endoscope.

Jpn. Pat. Appln. KOKAI Publication No. 7-20388 discloses a structure in which a stereoscopic image pickup unit is supported by a scope holder. The stereoscopic image pickup unit comprises a stereoscopic endoscope and stereoscopic camera. The scope holder is formed of a multi-joint arm having six or more degrees of freedom. The upper end of the multi-joint arm is fixed to the ceiling of an operating theater, and the lower end is attached to the stereoscopic image pickup unit.

Further, a display unit for displaying images picked by the endoscope is supported by a holder different from the scope holder.

An electromagnetic brake is incorporated in a joint between each pair of adjacent arm components of each holder. The electromagnetic brake is switched between a locked state and free state (unlocked state) by the operation of a switch. In the free state, the stereoscopic endoscope is movable, while in the locked state, it is kept immovable at an arbitrary position.

BRIEF SUMMARY OF THE INVENTION

The present invention provides a stereoscopic observation system comprising:

a stereoscopic optical unit provided with a pair of objectives for stereoscopic observation and optical devices corresponding to the respective objectives;

a stereoscopic camera connected to the stereoscopic optical unit, and used to pick up optical images formed by the optical devices, at least one of the stereoscopic camera and the optical unit serving as an instrument to be supported;

a support unit which supports the instrument; and a rotation mechanism incorporated in the support unit, the rotation mechanism having a rotary shaft substantially parallel to an optical axis of the objectives, the rotation mechanism supporting the instrument such that the instrument can rotate about an axis of the rotary shaft.

Preferably the rotation mechanism has limiting means of a frictional resistance type which applies a frictional force to the rotary shaft when the instrument is rotated, thereby limiting rotation of the instrument.

Preferably the support unit has at least one joint portion and engagement means to be engaged with the at least one joint portion mechanically and disengageably, and the rotation mechanism has an independent rotary portion which can rotate even if the engagement means is mechanically engaged with the at least one joint portion of the support unit.

Preferably the rotary shaft of the rotation mechanism is substantially coaxial with the optical unit.

Preferably the support unit incorporates a plurality of rotation mechanisms similar to the first-mentioned rotation mechanism.

Preferably the optical unit is a stereoscopic endoscope.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate an embodiment of the invention, and together with the general description given above and the detailed description of the embodiment given below, serve to explain the principles of the invention.

DETAILED DESCRIPTION OF THE INVENTION

Figure 1:
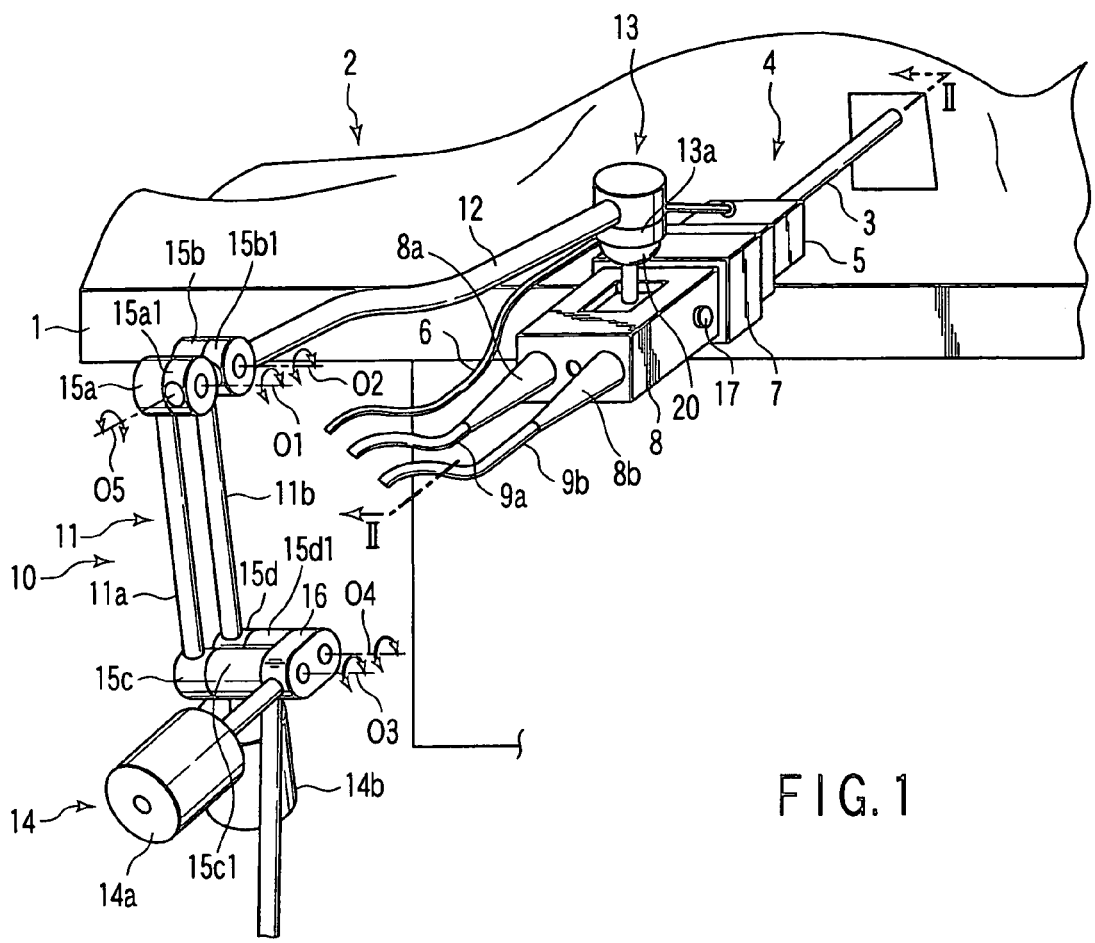
FIG. 1 is a schematic perspective view illustrating an essential part of a stereoscopic observation system according to a first embodiment of the invention.
Figure 3:
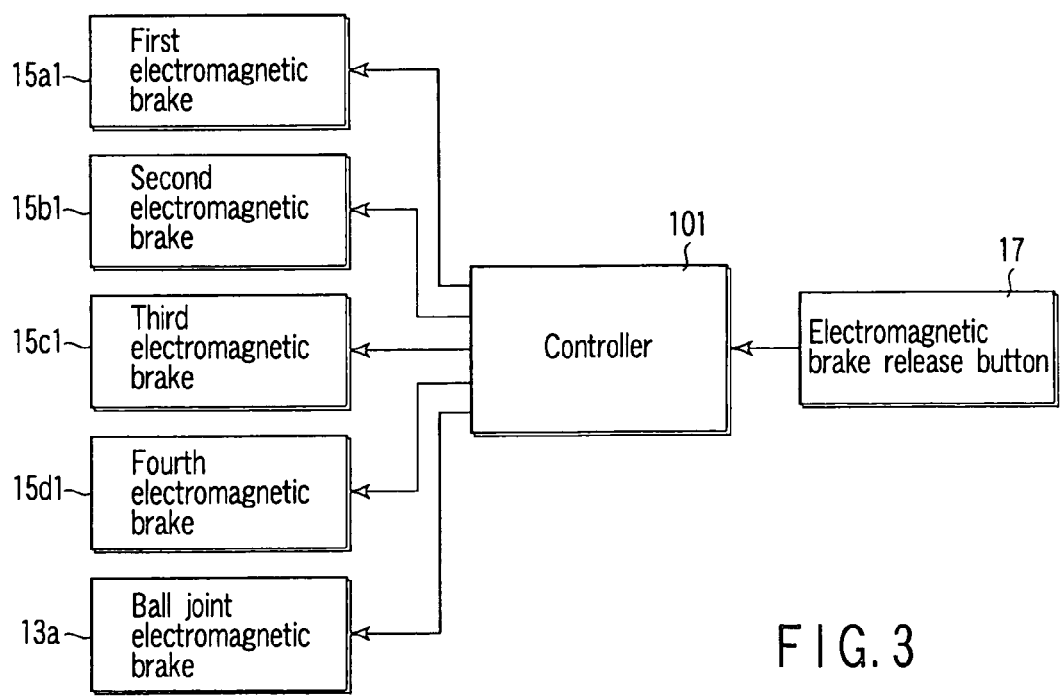
FIG. 3 is a block diagram useful in explaining the connected states of electromagnetic brakes incorporated in the stereoscopic observation system of the first embodiment.
Figure 2:
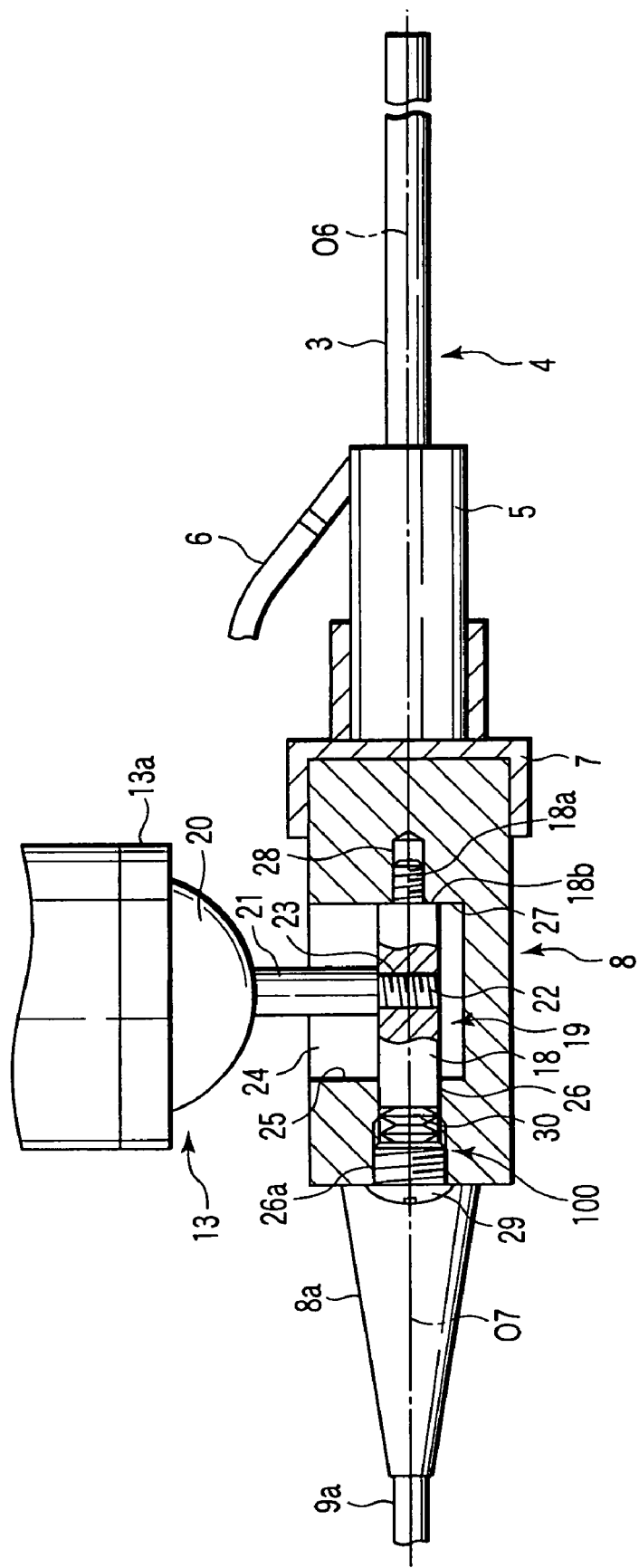
FIG. 2 is a sectional view taken along line II-II of FIG. 1, illustrating the junction between a stereoscopic camera and the ball-joint portion of a scope holder incorporated in the system of the first embodiment.

Referring first to FIGS. 1 to 3, a first embodiment of the invention will be described. FIG. 1 is a schematic perspective view illustrating an essential part of a stereoscopic observation system according to the first embodiment of the invention. In FIG. 1, reference numeral 1 denotes a surgery table, and reference numeral 2 a patient placed on the table 1 and to be subjected to an operation using an endoscope.

The stereoscopic observation system of the embodiment includes a stereoscopic endoscope 4 with a narrow insertion portion 3 to be inserted into the body of the patient 2 on the surgery table 1. The endoscope 4 contains an observation optical system for the right eye, and an observation optical system for the left eye, which are not shown. As a result, when the insertion portion 3 is inserted in the body cavity of the patient, the portion to be operated on can be observed three-dimensionally.

A hand-side operating portion 5 is provided at the proximal end of the insertion portion 3 of the endoscope 4. An end of a light guide 6 is coupled to the outer periphery of the operating portion 5, and the other end is coupled to a light source (not shown), so that the light needed for observation using the endoscope 4 is guided from the light source to the endoscope 4 via the light guide 6.

An eyepiece (not shown) is provided on the distal end of the operating portion 5, and connected to a stereoscopic camera 8 via a connection adapter 7. Thus, the endoscope 4 is connected to the stereoscopic camera 8 by the connection adapter 7.

Left and right image pickup sections 8a and 8b are contained in the stereoscopic camera 8, and are provided with respective image pickup elements. The image pickup elements of the image pickup sections 8a and 8b receive the images picked by the left and right observation optical systems of the endoscope 4, respectively.

An end of a cable 9a for the left eye and an end of a cable 9b for the right eye are coupled to the distal end of the stereoscopic camera 8. The other ends of the cables 9a and 9b are connected to respective camera control units (CCU) (not shown). The signals output from the two image pickup elements (not shown) in the stereoscopic camera 8 are transmitted to the respective camera control units via the cables 9a and 9b.

A scope holder (support unit) 10 is provided at a position near the surgery table 1. The scope holder 10 at least holds the endoscope 4 or the stereoscopic camera 8. The scope holder 10 mainly comprises a parallel link arm unit 11, extension arm 12 extending substantially horizontally, ball-joint portion 13 and counter weight 14.

The parallel link arm unit 11 includes two vertical arms 11a and 11b. The upper ends of the vertical arms 11a and 11b are coupled to an end of the extension arm 12 by means of couplers 15a and 15b, so that the vertical arms can rotate about an axis O1 and the extension arm can rotate about an axis O2.

Further, a lower arm 16 extending substantially horizontally is coupled to the lower ends of the vertical arms 11a and 11b by means of couplers 15c and 15d, so that the lower arm can rotate about axes O3 and O4.

Furthermore, the four shafts (not shown) of the couplers 15a to 15d included in the parallel link arm unit 11 are kept rotatable about the axes O1 to O4 in the directions indicated by the respective arrows. First to fourth electromagnetic brakes (lock mechanisms) 15a1 to 15d1, which can generate frictional forces for stopping the rotation of the shafts, are provided in the four couplers 15a to 15d, respectively. As shown in FIG. 3, the first to fourth electromagnetic brakes 15a1 to 15d1 are connected to a controller 101. In the normal state, the first to fourth electro-magnetic brakes 15a1 to 15d1 are activated to lock the four axels of the parallel link arm unit 11.

The stereoscopic camera 8 has an electromagnetic brake release button 17 for releasing the first to fourth electromagnetic brakes 15a1 to 15d1, and is connected to the controller 101. Only when the electromagnetic brake release button 17 is pushed, the first to fourth electromagnetic brakes 15a1 to 15d1 are released, thereby making the parallel link arm unit 11 movable.

The extension arm 12 is supported so that it can rotate about the axis O5 as indicated by the arrow in FIG. 1. An appropriate frictional force is imparted to the extension arm 12 so that the arm is not rotated about the axis O5 by the weight of the endoscope 4, stereoscopic camera 8 and connection adaptor 7 connected to the to-be-supported arm 12 by the ball-joint portion 13.

Further, the counter weight 14 comprises first and second counter weight components 14a and 14b. The first counter weight component 14a extends at one side of the lower arm 16. The second counter weight component 14b extends below the vertical arm 11b. The total weight of the counter weight components 14a and 14b is set to offset the total weight of the extension arm 12, endoscope 4, stereoscopic camera 8 and connection adaptor 7.

The ball-joint portion 13 is provided with a ball-joint electromagnetic brake 13a that has the same structure as the first to fourth electromagnetic brakes 15a1 to 15d1 provided in the respective shafts of the parallel link arm unit 11. The ball-joint electromagnetic brake 13a is also connected to the controller 101. The brake 13a provides a frictional force to the ball-joint portion 13 so that it is not rotated by the weight of the stereoscopic camera 8, endoscope 4, etc.

FIG. 2 is a schematic sectional view taken along line II-II of FIG. 1, illustrating the junction between the stereoscopic camera 8 and the ball-joint portion 13 of the scope holder 10. Specifically, FIG. 2 shows the portion between the left and right image pickup sections 8a and 8b, therefore does not show optical components, such as the image pickup elements and lens.

In this embodiment, a rotation mechanism 19 for a to-be-supported instrument is provided at the junction between the stereoscopic camera 8 and the ball-joint portion 13 of the scope holder 10. The rotation mechanism 19 has a rotary shaft 18 substantially parallel to the axis O6 of the insertion portion 3. The axis O7 of the rotary shaft 18 is set coaxial or substantially coaxial with the axis O6 of the insertion portion 3.

Further, a ball shaft 21 is formed integral with the ball 20 of the ball joint portion 13. A male screw portion 22 is formed at the tip of the ball shaft 21. A screw hole 23 is formed in the rotary shaft 18 in the direction perpendicular to the axis O6 of the insertion portion 3. The ball shaft 21 is secured to the rotary shaft 18 by screwing the male screw portion 22 of the ball shaft 21 of the ball joint portion 13 into the screw hole 23.

The stereoscopic camera 8 has a ball joint coupling hole 24 having an upper opening. An attachment hole 26 for attaching the rotary shaft 18 is formed in the side wall (the left wall in FIG. 2) 25 of the ball joint coupling hole 24 remote from the endoscope 4. The inner diameter of the attachment hole 26 is set so that the proximal end of the rotary shaft 18 can be fitted therein.

The rotary shaft 18 has a small-diameter shaft 18a at its distal end. A small-diameter hole 28 is formed in the side wall (the right wall in FIG. 2) 27 of the ball joint coupling hole 24 close to the endoscope 4 for receiving the small-diameter shaft 18a. The rotary shaft 18 is inserted in the ball joint coupling hole 24 of the stereoscopic camera 8, with a stepped portion 18b thereof kept in contact with the endoscope-side wall 27 of the coupling hole 24 located around the small-diameter hole 28.

Furthermore, a female screw portion 26a is formed in the outer end surface of the attachment hole 26 of the stereoscopic camera 8. A pressing screw 29 that holds the rotary shaft 18 is screwed in the female screw hole 26a. Four plate springs 30 are interposed between the pressing screw 29 and rotary shaft 18 in the attachment hole 26. The stepped portion 18b of the rotary shaft 18 is pressed against the wall 27 around the small-diameter hole 28 with the four plate springs 30 interposed therebetween, by screwing the pressing screw 29 into the female screw portion 26a. This structure provides a frictional force to the rotary shaft 18. This frictional force is set to a value that prevents the rotary shaft 18 from being rotated about the axis O6 by the weight of the stereoscopic camera 8, connection adaptor 7 and endoscope 4, but that permits the shaft 18 to easily rotate about the axis O6 when an appropriate rotational force (not so strong force) is applied thereto from the outside. Thus, the above structure provides frictional engagement means (limiting means) 100 that holds the rotation mechanism 19 so that the supported instrument can rotate about the rotary shaft 18 even if the first to fourth electromagnetic brakes 15a1 to 15d1 are locked, when a force of rotation greater than the above-mentioned frictional force is applied to the supported instrument.

The operation of the above structure will now be described. When the stereoscopic observation system of the embodiment is used, a surgeon performs an operation while observing the interior of the body cavity of a patient 2 using the endoscope 4. At this time, if the surgeon pushes the electromagnetic brake release button 17 of the stereoscopic camera 8, the first to fourth electromagnetic brakes 15a1 to 15d1 and electromagnetic brake 13a are released, thereby making, movable, the parallel link arm unit 11, extension arm 12 and ball joint portion 13 of the scope holder 10. In this state, the insertion portion 3 of the endoscope 4 is inserted into the body cavity of the patient 2, and guided to a desired observation position.

After guiding the endoscope 4 to the desired observation position, the first to fourth electro-magnetic brakes 15a1 to 15d1 and electromagnetic brake 13a are again operated by losing surgeon's hold of the electromagnetic brake release button 17. As a result, the endoscope 4 is switched to the locked state in which the endoscope 4 odes not spontaneously move at the observation position.

In this state, an operation is performed using an instrument (not shown), while observing a stereoscopic image displayed on the display (not shown) of the endoscope 4. At this time, it is necessary to position the stereoscopic camera 8 in a correct position. In the correct position, the straight line obtained by connecting the image pickup elements of the left and right image pickup sections 8a and 8b of the camera 8 on a plane perpendicular to the axis O6 of the insertion portion 3 of the endoscope 4 is substantially parallel to the straight line obtained by connecting the eyes of the surgeon. If the camera 8 is not positioned in a correct position, it is difficult for the surgeon to manipulate the instrument while observing a stereoscopic image on the display.

Therefore, if the stereoscopic camera 8 is not positioned in a correct position, it is necessary to rotate the endoscope 4 about the axis O6 of the insertion portion 3 and situate the endoscope in a position in which the surgeon can feel the image on the display natural and perform an operation without feeling fatigue. In the embodiment, during this operation, the surgeon rotates the stereoscopic camera 8 about the axis O6 of the insertion portion 3, while gripping the endoscope 4 without pushing the electro-magnetic brake release button 17. Since at this time, the ball joint portion 13 is locked by the electro-magnetic brake 13a, the ball shaft 21 is kept immovable. Therefore, the stereoscopic camera 8 rotates in the same direction as the rotation direction of the rotary shaft 18.

As mentioned above, the stepped portion 18b of the rotary shaft 18 is pressed by the plate springs 30 against the side wall 27 of the ball joint coupling hole 24 close to the endoscope 4, whereby the rotary shaft 18 is prevented from being rotated by the weight of the endoscope 4, stereoscopic camera 8, etc. Accordingly, if the surgeon loses their hold of the stereoscopic camera 8 after rotating the camera 8 through a desired angle, the camera 8 stops at the angle. Thus, the camera 8 can be positioned correctly, thereby providing an optimal stereoscopic image.

The above-described structure provides the following advantage. In the embodiment, the rotation mechanism 19 for rotating a supported instrument, which has the rotary shaft 18 substantially parallel to the axis O6 of the insertion portion 3 of the endoscope 4, is provided at the junction between the scope holder 10 and the stereoscopic camera 8 as the supported instrument. The rotation mechanism 19 has the plate springs 30 and pressing screw 29 that press the rotary shaft 18 to prevent the rotation of the supported instrument. The embodiment also incorporates the frictional engagement means 100 that holds the rotation mechanism 19 so that the supported instrument can rotate about the rotary shaft 18 even if the scope holder 10 is locked, when a force of rotation greater than the pressing force of the plate springs 30 is applied to the instrument. Therefore, if the stereoscopic camera 8 is not positioned in a correct position, it can be adjusted by rotating the endoscope 4 about the axis O6 of the insertion portion 3 with the scope holder 10 fixed, i.e., with the tip of the endoscope 4 kept immovable. This enables a surgeon to easily and quickly observe an optimal stereoscopic image.

To position the stereoscopic camera 8 in a correct position, assume that the electromagnetic brake release button 17 is pushed to release the first to fourth electromagnetic brakes 15a1 to 15d1 and electromagnetic brake 13a and make the endoscope 4 movable. In this case, the tip of the endoscope 4, which is positioned in an optimal position, may well be deviated therefrom when the endoscope 4 is rotated about its axis. At this time, the working has to be retraced from the positioning of the tip of the endoscope 4, which is very troublesome.

On the other hand, if, as in the embodiment, the stereoscopic camera 8 is adjusted by rotating the endoscope 4 about the axis O6 of the insertion portion 3 with the scope holder 10 fixed, the working of positioning the tip of the endoscope 4 can be omitted. Thus, the position adjustment of the endoscope 4 can be easily performed in a short time.

Furthermore, in the embodiment, after the endoscope 4 supported by the scope holder 10 is positioned by operating the holder 10 close to a portion to be operated on, the angular position of the endoscope 4 can be easily adjusted without again operating the scope holder 10, thereby reducing the time required for a surgical operation.

Figure 4:
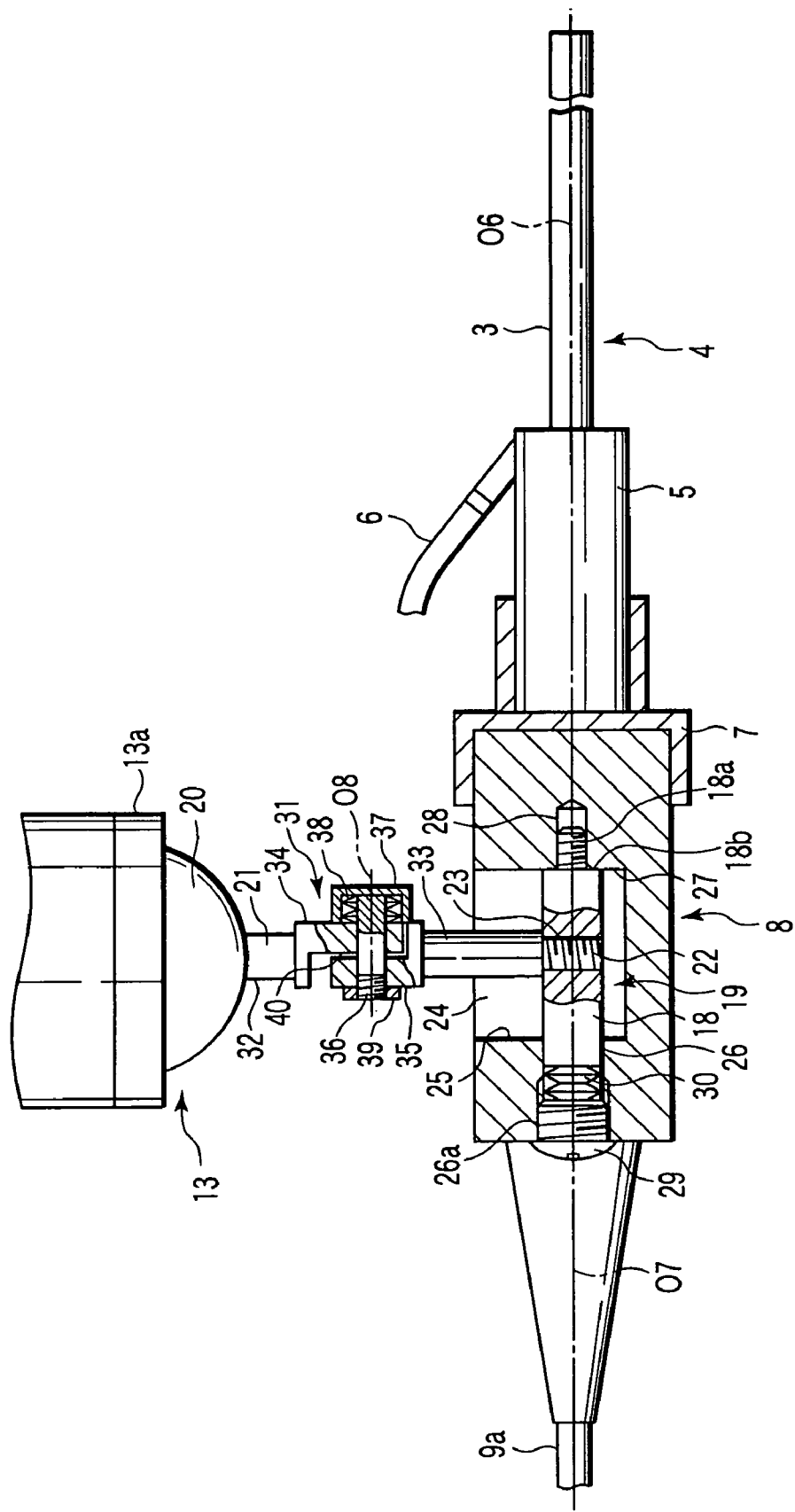
FIG. 4 is a longitudinal sectional view, illustrating the junction between a stereoscopic camera and the ball-joint portion of a scope holder incorporated in a stereoscopic observation system according to a second embodiment.

FIG. 4 shows a second embodiment of the invention. The second embodiment is obtained by modifying, in the manner described below, the junction between the stereoscopic camera 8 and the ball joint portion 13 of the scope holder 10 employed in the first embodiment shown in FIGS. 1 to 3. In FIG. 4, elements similar to those in the first embodiment are denoted by corresponding reference numerals, and no description is given thereof.

In the second embodiment, a join portion 31 is provided across the middle portion of the ball shaft 21 of the ball joint portion 13. The ball shaft 21 is divided into a first link arm 32 close to the ball joint portion 13, and a second link arm 33 close to the stereoscopic camera 8. L-shaped couplers 34 and 35 are secured to the tips of the link arms 32 and 33, respectively.

In the joint portion 31, the L-shaped couplers 34 and 35 oppose each other. Further, a joint shaft 36 substantially parallel to the axis O6 of the insertion portion 3 of the endoscope 4 is inserted through the L-shaped couplers 34 and 35. The link arms 32 and 33 are coupled to the joint portion 31 so that they can rotate about the axis O8 of the joint shaft 36.

A spring holder 37 is secured to an end of the joint shaft 36. Four plate springs (urging means) 38 are inserted in the spring holder 37. A male screw portion is provided on the other end of the joint shaft 36. A nut 39 is screwed on the male screw portion. A washer 40 is provided at the slide portion between the L-shaped couplers 34 and 35. When the nut 39 is fastened, the urging force of the four plate springs 38 is exerted upon the slide portion between the L-shaped couplers 34 and 35 and washer 40, so that the link arms 32 and 33 can rotate about the axis O8 of the joint shaft 36 by an appropriate sliding frictional force. The appropriate sliding frictional force means a frictional force that prevents the link arms 32 and 33 from being rotated by the weight of the endoscope 4, stereoscopic camera 8, etc., and that enables a surgeon to easily rotate the link arms.

The operation of the second embodiment will be described. When the stereoscopic observation system of the embodiment is used, a surgeon pushes the electro-magnetic brake release button 17 of the stereoscopic camera 8 to switch the parallel link arm unit 11, extension arm 12 and ball joint portion 13 movable. In this state, the insertion portion 3 of the endoscope 4 is inserted into the body cavity of a patient 2 and guided to a desired observation position.

After the tip of the endoscope 4 is guided to a desired observation position, the surgeon loses their hold of the electromagnetic brake release button 17, thereby locking the electromagnetic brakes. As a result, the endoscope 4 is prevented from spontaneously moving. In this state, observation is started.

If it is necessary to change the to-be-observed portion while performing a treatment using a stereoscopic image, therefore to slightly move the tip of the endoscope 4, the surgeon slightly moves the tip of the endoscope 4 to the next target portion while gripping the stereoscopic camera 8. At this time, since the electromagnetic brake release button 17 is not pushed, the scope holder 10 is kept fixed. Accordingly, the endoscope 4 does not move in the direction of the optical axis, and only the angular position of the endoscope 4 can be slightly changed with the focal point maintained as it is.

In addition, to realize an appropriate stereoscopic image as in the first embodiment, the endoscope 4 can be rotated about the axis O6 of the insertion portion 3.

As stated above, in the second embodiment, to perform stereoscopic observation as in the first embodiment, the endoscope 4 can be rotated about the axis O6 of the insertion portion 3, with the scope holder 10 fixed. Further, in the second embodiment, in particular, the tip of the endoscope 4 can be made immovable in the direction of the optical axis, and movable only in the plane substantially perpendicular to the optical axis. This prevents the stereoscopic camera from becoming out of focus after the observation position is changed.

Figure 5:
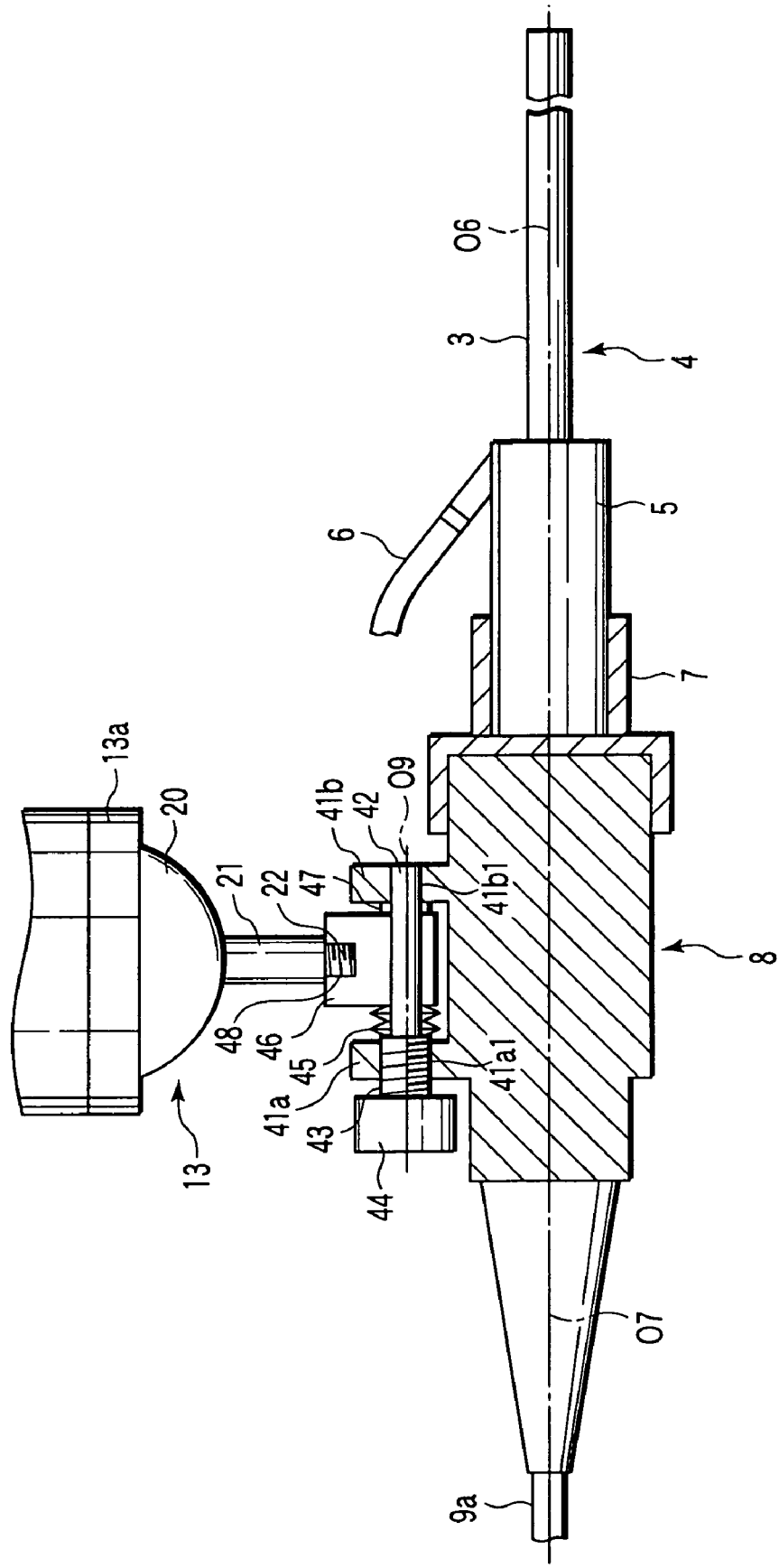
FIG. 5 is a longitudinal sectional view, illustrating the junction between a stereoscopic camera and the ball-joint portion of a scope holder incorporated in a stereoscopic observation system according to a third embodiment.

FIG. 5 shows a third embodiment of the invention. The third embodiment is obtained by modifying, in the manner described below, the junction between the stereoscopic camera 8 and the ball joint portion 13 of the scope holder 10 employed in the first embodiment shown in FIGS. 1 to 3. In FIG. 5, elements similar to those in the first embodiment are denoted by corresponding reference numerals, and no description is given thereof.

Specifically, in the third embodiment, a pair of bearings 41a and 41b project from the outer periphery of the stereoscopic camera 8. A rotary shaft 42 is held between the bearings 41a and 41b. The axis O9 of the rotary shaft 42 is substantially parallel to the axis O6 of the insertion portion 3 of the endoscope 4. The bearing 41a has a screw hole 41a1, while the other bearing 41b has a shaft support hole 41b1.

A male screw portion 43 is formed on an end of the rotary shaft 42. The male screw portion 43 is screwed in the screw hole 41a1 of the bearing 41a. A knob 44 is provided at the distal end of the male screw portion 43, and is formed integral with the rotary shaft 42. The other end of the rotary shaft 42 is fitted in the shaft support hole 41b1 of the bearing 41b. Thus, the other end of the rotary shaft 42 is supported by the bearing 41b so that it can rotate about the axis O9 of the rotary shaft 42.

Plate springs 45, block 46 and washer 47 are provided on the rotary shaft 42 between the bearings 41a and 41b. The block 46 is fitted on the rotary shaft 42 so that it can slide and rotate. When the knob 44 is rotated, the rotary shaft 42 advances or retracts along the axis O6. The sliding resistance between the block 46 and rotary shaft 42 can be adjusted by pushing or pulling the block 46 using the pressing force of the plate springs 45.

A screw hole 48 is formed in the block 46 in the direction perpendicular to the axis O9 of the rotary shaft 42. The ball shaft 21 is attached to the rotary shaft 42 by screwing the male screw portion 22 of the ball shaft 21 of the ball joint portion 13 into the screw hole 48.

The operation of the third embodiment constructed as above will be described. When the stereoscopic observation system of the third embodiment is used, it may become necessary to rotate the endoscope 4 to enable a surgeon to perform appropriate stereoscopic observation. In this case, the surgeon grips the stereoscopic camera 8, and rotates the endoscope 4 about the axis O9 of the rotary shaft 42 in a desired direction. If the surgeon feels that the force required to rotate the endoscope 4 is inappropriate, they can adjust it by rotating the knob 44.

Moreover, in the third embodiment, the surgeon can make the endoscope 4 immovable about the axis O9 of the rotary shaft 42 by rotating the knob 44 and increasing the pressing force of the plate springs 45.

The above-described third embodiment provides the following advantages. Firstly, the endoscope 4 can be rotated about the axis O9 of the rotary shaft 42 for enabling appropriate stereoscopic observation, even if the scope holder 10 is fixed, as in the first embodiment. Secondly, the force required to rotate the endoscope 4 about the axis O9 of the rotary shaft 42 can be adjusted to a value surgeons wish, by rotating the knob 44 to adjust the sliding resistance between the block 46 and rotary shaft 42.

Although in the third embodiment, the bearings 41a and 41b are formed integral with the exterior package of the stereoscopic camera 8, they may be formed separate from the package so that they can be detached therefrom. In this case, it is sufficient if the bearings 41a and 41b are attached to the package, only when the above function is needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A stereoscopic observation system comprising:
a stereoscopic optical unit provided with a pair of objectives for stereoscopic observation and optical devices corresponding to the respective objectives;

a stereoscopic camera connected to the stereoscopic optical unit, and operable to pick up optical images formed by the optical devices, at least one of the stereoscopic camera and the stereoscopic optical unit serving as an instrument to be supported;

a support unit which supports the instrument; and a rotation mechanism disposed at a distal end of the support unit, the rotation mechanism having an independent rotary shaft substantially parallel to an optical axis of the objectives, the rotation mechanism supporting the instrument such that the instrument can rotate about an axis of the independent rotary shaft;

the support unit comprising at least one movable portion and an engagement unit adapted to disengageably engage with the at least one movable portion, the movable portion adapted to allow a movement of the instrument when the engagement unit is mechanically disengaged from the movable portion, and the rotation mechanism comprising the independent rotary shaft operable to rotate without allowing a non-rotational movement of the instrument even when the engagement unit is engaged with the at least one movable portion.

2. The system according to claim 1, the rotation mechanism comprising a limiting pressure unit of a frictional resistance type structured to apply a frictional force to the rotary shaft when the instrument is rotated, thereby limiting rotation of the instrument.

3. The system according to claim 1, wherein the independent rotary shaft of the rotation mechanism is substantially coaxial with the optical unit.

4. The system according to claim 1, wherein the support unit incorporates an additional rotation mechanism.

5. The system according to claim 1, wherein the optical unit is a stereoscopic endoscope.

* * * * *